United States Patent [19]

Dorman et al.

[11] 3,966,701

[45] June 29, 1976

[54] FIBRINOGEN PEPTIDE DERIVATIVES

[75] Inventors: Linneaus C. Dorman; Roberta C. Cheng, both of Midland, Mich.

[73] Assignee: The Dow Chemical Company, Midland, Mich.

[22] Filed: Nov. 7, 1973

[21] Appl. No.: 413,745

[52] U.S. Cl. .......................... 260/112.5 R; 424/177
[51] Int. Cl.² .................. C07C 103/52; C08H 1/00; A61K 37/00
[58] Field of Search ................... 260/112.5; 424/177

[56] References Cited
UNITED STATES PATENTS 3,778,426  12/1973  Najjar ............................ 260/112.5

FOREIGN PATENTS OR APPLICATIONS 1,924,802  11/1970  Germany

OTHER PUBLICATIONS

Robinson: *Arch. Biochem, Biophys.,* 122, 516–518 (1967).

Dorman et al.: "Chemistry and Biology of Peptides," J. Meienhofer, ed., Ann Arbor Science Pub., Ann Arbor, Mich., 1972, pp. v–viii, 455–459.

*Primary Examiner*—Lewis Gotts
*Assistant Examiner*—Reginald J. Suyat
*Attorney, Agent, or Firm*—Theodore Post; C. Kenneth Bjoch

[57] ABSTRACT

Fibrinogen peptide derivatives which have biological activity as anticoagulants of blood having the dipeptide moiety prolylarginine or the tripeptide moiety glycylprolylarginine, e.g., L-prolyl-L-arginine benzyl ester p-toluenesulfonate trifluoroacetate, glycyl-L-prolyl-L-arginine benzyl ester p-toluenesulfonate trifluoroacetate, N-t-butyloxycarbonyl-L-prolyl-L-arginine benzyl ester p-toluenesulfonate methanolate, N-benzyloxycarbonyl-prolyl-L-arginine benzyl ester p-toluenesulfonate methanolate and N-t-butyloxycarbonylglycol-L-prolyl-L-arginine benzyl ester p-toluenesulfonate.

7 Claims, No Drawings

FIBRINOGEN PEPTIDE DERIVATIVES

BACKGROUND OF THE INVENTION

In the clotting of blood, the α- and β-chains of blood protein fibrinogen is cleaved at the Arg-Gly (arginyl glycine) bonds by the enzyme thrombin, producing fibrin which polymerizes and is subsequently cross-linked enzymatically to form a permanent blood clot. The art suggests that the specificity of the thrombin-fibrinogen reaction is attributable to the amino acid sequence of the α- and β-chains of fibrinogen, particularly in the vicinity of the Arg-Gly bonds. In the synthesis of the 14–22 sequence of the α(A) chain of human fibrinogen for study of its activity, i.e., binding and cleavage, toward the enzyme thrombin, analogs and fragments of this nonapeptide were synthesized in order to assess how activity toward thrombin would vary with change or alteration of structure.

SUMMARY OF THE INVENTION

In the course of the research leading to this invention, biological screeing revealed that certain novel derivatives of the tripeptide, Gly-Pro-Arg (glycyl-prolylarginine) exhibited substantial anticoagulant activity in vitro. While the tripeptide itself was known, and was found to occur in the α(A) chain of the fibrinogen of many mammalian species, derivatives of this invention were not previously known. It was also discovered as part of this invention that some derivatives of the dipeptide, pro-Arg(prolylarginine) were compounds to have high in vitro anti-coagulant activity. The new cmpounds of this invention, then, encompass protected Pro-Arg dipeptides and protected Gly-Pro-Arg tripeptides and their salts with a pharmaceutically acceptable acid (the anions of which are relatively innocuous to mammals at dosages consistent with good biological activity of said salts) and, when recovered from methanol, may be solvated with methanol, e.g., a member of the group consisting of L-prolyl-L-arginine benzyl ester p-toluenesulfonate trifluoroacetate, glycyl-L-prolyl-L-arginine benzyl ester p-toluenesulfonate trifluoroacetate, N-t-butyloxycarbonyl-L-prolyl-L-arginine benzyl ester p-toluenesulfonate methanolate, N-benzyloxycarbonyl-L-prolyl-L-arginine benzyl ester p-toluenesulfonate methanolate and N-t-butyloxycarbonylglycyl-L-prolyl-L-arginine benzyl ester p-toluenesulfonate, and similarly protected peptides and their salts. The protective groups used in the synthesis of products of this invention are those conventionally used in polypeptide synthesis for protecting amino and carboxylic acid groups. Representative protective groups are indicated in the preparative examples.

Since simple peptides and their derivatives are readily degradable, e.g., to amino acids, the compounds of this invention would be expected to be less toxic than heparin and coumarin derivatives in animal therapy. Also, their effects as anticoagulants are shorter-lived than coumarin or heparin or their derivatives, hence the probability of excessive bleeding should be easier to control.

DESCRIPTION OF THE PREFERRED EMBODIMENTS

The following additional description and examples further describe the invention and the manner and process of making and using it to enable the art skilled to make and use the same and set forth the best mode contemplated by the inventors of carrying out the invention.

PREPARATION A: ARGININE BENZYL ESTER DI-P-TOLUENESULFONATE

A stirred mixture of 8.7 g. (0.05 mole) of L-arginine, 20.9 g. (0.11 mole) of p-toluenesulfonic acid monohydrate, 125 ml. of benzyl alcohol and 130 ml. of benzene was refluxed for ca. 18 hours. Azeotropic removal of water was facilitated by the use of a Dean-Stark trap. The reaction mixture was decanted from the reaction vessel while still warm and diluted with ethyl acetate, precipitating the product as a white hygroscopic solid. The product was collected on a sintered glass funnel while it was protected from atmospheric moisture by a solvent blanket consisting first of a solution of benzyl alcohol and ethyl acetate, then ethyl acetate and finally ether. The ether-damp solid was then dried in the funnel in a vacuum desiccator over Drierite desiccant. There was obtained 26 g. (85%) of white solid which had a neutral equivalent of 598 vs. theory of 609. Infrared (Nujol mull): $\nu$, 3180 and 3280 (N-H), 2700 ($\equiv N^+—H$), 1755 ($>C=O$, ester)$cm^{+1}$. Exposure of the product to air resulted first in liquefaction followed by crystallization of the hydrate, m.p. 66°–67.5°C., $[\alpha]_D^{25}$ + 2.16 (c.1.946, ethanol), N.E. 627 (theory 627).

Anal. Calcd for $C_{27}H_{36}N_4O_8S_2.H_2O$: C,51.74; H,6.11; N, 8.94; S, 10.23. Found: C, 51.47; H, 6.07; N, 8.85; S,9.94.

EXAMPLE 1:
N-t-Butyloxycarbonyl-L-prolyl-L-arginine Benzyl Ester p-Toluenesulfonate Methanolate A. Dicyclohexylcarbodiimide Coupling Procedure A stirred mixture of 11.0 g. (0.018 mole) of arginine benzyl ester di-p-toluenesulfonate, 2.08 g. (0.018 mole) of N-hydroxysuccinimide, 3.90 g. (0.0181 mole) of N-t-butyloxycarbonyl-L-proline and 100 of acetonitrile was treated with 2.52 ml. (0.0181 mole) of triethylamine. This mixture was then cooled to 0°C. whereupon a solution of 3.75 g. (0.0181 mole) of dicyclohexylcarbodiimide in ca. 10 ml. of acetonitrile was added. Stirring in the cold was continued for 3 hours and at room temperature for 48 hours. Precipitated dicyclohexylurea (3.8 g., 94%) was removed by filtration and washed with acetonitrile. The combined filtrate and wash was freed of solvent in vacuo and the residue was partitioned between 100 ml. portions of methylene chloride and water. The organic layer was separated, washed again with water, dried over $Na_2SO_4$ and Drierite desiccant and freed exhaustively of solvent. There was left as the residue 11.9 g. of white amorphous, foam-like solid. This solid, 10.6 g., was stirred in 200 ml. of ether, and the mixture was filtered. Evaporation of the filtrate left 10.0 g. of amorphous foam-like solid. A 2.0 g. portion of this was heated in 80–100 ml. of benzene and filtered; evaporation of the filtrate left 1.8 g. of white solid (same appearance as observed previously) of which 1.5 g. was chromatographed on a column (2.2 (O.D.) × 30 cm) of silica gel which was prepared with methylene chloride. The column was eluted with 100 ml. of methylene chloride, then a mixture of methylene chloride and methanol (4:1, v/v). There was recovered from the main fraction, 1.2 g., of purified product. Tlc($SiO_2$; 250 $\mu$,n-BuOH:AcOH:$H_2O$, 3:1:1):

U.V. sensitive, $R_f$ 0.77 (p-toluenesulfonic acid), 0.87 (dipeptide product); chlorination (t-BuOCl/KI plus o-tolidine) sensitive, $R_f$ 0.87; ninhydrin sensitive, none. $[\alpha]_D^{25}$ — 40.3°C.(c 2.07, ethanol). Nmr (DMSO-D$_6$(DMSO-d— 1.34 (singlet, (CH$_3$)$_3$C—), —1.72 (cluster,

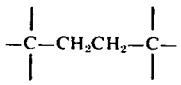

in Pro and Arg), —2.31 (singlet,

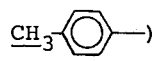

, —3.20 (cluster, —CH$_2$—N in Pro and Arg), —3.46 (singlet CH$_3$OH), —4.2 (cluster, α-methinyl protons in Pro and Arg), —5.13 (singlet,

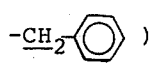

—7.15 and —7.58 (doublets of p-toluenesulfonic acid ring protons superimposed over some —N—H's) —7.36 (singlet, ring protons of benzyl function) ppm (TMS).

Anal. Calcd. for C$_{23}$H$_{35}$N$_5$O$_5$·CH$_3$C$_6$H$_4$SO$_3$H·CH$_3$OH: C, 55.9; H, 7.1; N, 10.5; S, 4.82. Found: C, 56.4; H, 6.8; N, 10.9; S, 4.98.

B. Mixed Anhydride Coupling Procedure

To a stirred mixture of 10.8 g. (0.05 mole) of N-t-butyloxycarbonyl-L-proline and 100 ml. of methylene chloride protected from atmospheric moisture was added a solution of 6.84 g. (0.05 mole) of i-butyl choroformate in 10 ml. of methylene chloride. This mixture was cooled to —20°C. whereupon a solution of 5.06 g. (0.05 mole) of N-methylmorpholine in 10 ml. of methylene chloride was added dropwise during 3–5 minutes, the reaction temperature being maintained at ≤ —15°C. Five minutes after the addition was completed a cold (ca. 5°C.) solution of 31.2 g. (0.05 equivalent) of L-arginine benzyl ester di-p-toluenesulfonate and 5.06 g. (0.05 mole) of N-methylmorpholine in ca. 150 ml. of methylene chloride was added in small portions to the well-stirred reaction mixture, the temperature being controlled between —15° to —10°C. After the addition, stirring was continued at —17° to —13°C. for 30 minutes, —13° to —7°C. for 45 minutes and then allowed to warm slowly to room temperature and stir overnight. The opaque reaction mixture was washed (2 × 100 ml.) with water, dried (MgSO$_4$), filtered through diatomaceous earth and evaporated to dryness in vacuo leaving 32.6 g. of cream-white, amorphous, foam-like solid as the residue. This was triturated in 150 ml. of water, then partitioned between 250 ml. of methylene chloride. The organic layer was separated, dried (MgSO$_4$), treated with Darco activated carbon and evaporated to dryness in vacuo leaving 31.3 g. of white foam-like solid. This was powdered and stirred under 390 ml. of ether overnight; the ether was decanted and the solid washed with ether by decantation and dried by yielding 29.3 g. of product which was finally purified as previously by chormatography on a column (6.5 × 56 cm) of silica gel. The column was eluted first with ca. 1 l. of methylene chloride and thereafter with methylene chloridemethanol (9:1 v/vFractions 1–14 (200 ml.) were free of any material; fractions 15–21 (150 ml.) contained, after evaporation, 0.1, 8.1, 4.8, 3.7, 1.6, 0.5 and 0.2 g., respectively; fractions 16–20 left characteristically white, amorphous foam-like solids which were shown by thin-layer chromatography to be homogeneous and identical to the product of part A. Nmr spectra were also identical to that of the product of part A. Total yield, 18.7 g. (56%).

EXAMPLE 2: L-Prolyl-L-arginine Benzyl Ester p-Toluenesulfonate Trifluoroacetate

N-t-Butyloxycarbonyl-L-prolyl-L-arginine p-toluenesulfonate methanolate, 3.7 g. (5.55 mmoles), was stirred in 25 ml. of a solution of methylene chloride-trifluoroacetic acid (2:3 v/v) containing 1% anisole while protected from moisture. After 25 minutes, the solution was evaporated in vacuo at room temperature. Ether was added to the concentrate and the mixture was evaporated again. The residue was dissolved in 40–50 ml. of methylene chloride and diluted to 200 ml. with ether. Resulting crystallization of the product was facilitated by scratching then cooling. The product was collected on sintered glass, washed with methylene chloride-ether solution and ether, and dried to yield 2.8 g. (78%) of white solid. Nmr spectrum of the product was essentially like that of the starting material, except for the absence of the t-butyl and the methyl (methanol absorptions. $[\alpha]_D^{25}$ —25.2 (c 1.092, ethanol).

Anal. Calcd. for C$_{18}$H$_{25}$N$_5$O$_5$·CH$_3$C$_6$H$_4$SO$_3$H·CF$_3$CO$_2$H: C, 50.1; H, 5.60; N, 10.8; Found: C, 49.9; H, 5.42; N, 10.6.

EXAMPLE 3:
N-t-Butyloxycarbonylglycyl-L-prolyl-L-arginine Benzyl Ester p-Toluenesulfonate To a stirred solution of 12.0 g. (0.02 equiv.) of L-prolyl-L-arginine benzyl ester p-toluenesulfonate trifluoroacetate, 3.6 (Neut. Equiv. =598), 3.6 g. (0.0206 mole) of N-t-butyloxycarbonylglycine, and 2.05 g. (0.0203 mole) of triethylamine in 90 ml. of methylene chloride at — 5°C. was added in portions a solution of 4.2 g. (0.0203 mole) of dicyclohexylcarbodiimide in 20 ml. of methylene chloride. Stirring was continued at —5° to 0°C. for 1.5 hours, then allowed to warm slowly to room temperature and stir overnight. After removal of dicyclohexylurea by filtration, the filtrate and wash were evaporated and the residue was partitioned between 50 ml. of water and 125 ml. of methylene chloride. The organic layer was separated, dried (MgSO$_4$) and evaporated leaving 14.2 g. of white gelatinous solid. This was dissolved in 85 ml. of benzene, filtered through diatomaceous earth and the filtrate was diluted with 300 ml. of ether which caused the separation of a semi-solid mass. When settling was complete, the mixture was decanted and the residue was triturated with ether causing complete solidification of the mass. The solid was collected, washed with ether, dried at room temperature under modest vacuum, then at 50–55°C. in a vacuum oven. Obtained 12.6 g. of white powder-like solid. Nmr (DMSO-d$_6$): —1.37 (sharp singlet, (CH$_3$)$_3$C—), —1.8 (cluster,

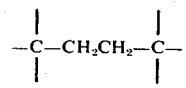

in Pro and Arg), —2.3 (singlet,

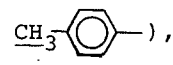

ca. −3.5 (cluster,

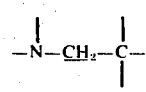

of Pro and Arg and CH₂ of Gly), −4.35 (cluster, α-methinyl protons), −5.13 (singlet,

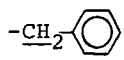,

−7.35 (singlet, benzyl ring protons), −7.18 and −7.61 (doublets, ring protons of

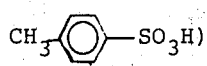

ppm (TMS).

EXAMPLE 4: Glycyl-L-Prolyl-L-Arginine Benzyl Ester p-Toluenesulfonate Trifluoroacetate N-t-Butyloxycarbonylglycyl-L-prolyl-L-arginine benzyl ester p-toluenesulfonate, 2.1 g., was stirred in 20 ml. of methylene chloride-trifluoroacetic acid (3.2 v/v) containing 1% anisole with exclusion of moisture for 20 minutes. After evaporation, the residue was dissolved in 20 ml. of methylene chloride, filtered and the filtrate was diluted with ca. 50 ml. of ether. A semi-solid separated which failed to crystallize on refrigeration. The supernatant was decanted and ether was added to the residue. Trituration led to crystallization and the product was collected, washed well with ether, then dried in vacuo at 50°C. and at room temperature to yield 1.95 g., $[\alpha]_D^{25}$ −41.7°C. (c 0.992, ethanol).

Anal. Calcd. for $C_{20}H_{30}N_6O_6 \cdot CH_3C_6H_4SO_3H \cdot CF_3CO_2H$: C, 49.9; H, 5.38; N, 11.9. Found: C, 49.4; H, 5.51; N, 11.9.

EXAMPLE 5:
N-Benzyloxycarbonyl-L-prolyl-L-arginine Benzyl Ester p-Toluenesulfonate Methanolate To a stirred mixture of 6.0 g. (0.0241 mole) of benzyloxycarbonyl-L-proline and 100 ml. of methylene chloride protected from atmospheric moisture was added at ca. 10°C. a solution of 3.3 g. (0.0241 mole) of i-butyl chloroformate in 10 ml. of methylene chloride. This mixture was cooled to −20°C. whereupon a solution of 2.43 g. (0.0241 mole) of N-methylmorpholine in 5 ml. of methylene chloride was added dropwise during 6 minutes, the reaction temperature being maintained between −20°C. to −15°C. Five minutes later, an opaque solution of 15.8 g. (0.0253 equivalent) of L-arginine benzyl ester di-p-toluenesulfonate and 2.56 g. (0.0253 mole) of N-methylmorpholine in ca. 120 ml. of methylene chloride, pre-cooled at −5°C., was added in small portions such that the reaction temperature could be maintained between −15° to −10°C. Stirring and cooling at −15° to −10°C. was continued for two hours, then the reaction mixture was allowed to warm to room temperature and stir overnight. The opaque reaction mixture was washed successively with water, dilute salt solution and saturated salt solution, dried over MgSO₄, treated with Darco activated carbon and diatomaceous earth and filtered. Removal of solvent from the filtrate in vacuo at ≤45°C. left 15.7 g. of amber semi-solid mass as the residue which was then chromatographed on a column (2.5 × 60 cm.) of silica gel. The column was eluted successively with methylene chloride (800 ml.), methylene chloride containing 1% (400 ml.), 3% (400 ml.) and 5% (1300 ml.) methanol. Fractions 1–10 (200 ml.) were void of any material. Fractions 11–22 (75 ml.) were examined by tlc (SiO₂; 250 μ, n-BuOH-:AcOH:H₂O,3:1:1). Fractions 15–19 were homogeneous (R_f 0.76, I₂ sensitive) and yielded, after evaporation, a total of 4.6 g. (fractions 14, 20, 21 and 22 were slightly contaminated, yielding 2.8 g. after evaporation). $[\alpha]_d^{25}$ −43.3°C. (c 1.20, ethanol). Nmr (DMSO-d₆): −1.75 (cluster,

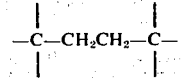

in Pro and Arg), −2.08 (singlet, —OH of methanol), −2.19 (singlet

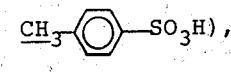,

−3.08 (cluster,

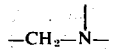

in Pro and Arg), −3.35 (singlet CH₃OH), −4.28 (cluster, α-methinyl H's in Pro and Arg), −5.03 and −5.13 (benzyl —CH₂—'s). −7.16 and −7.58 (doublets of p-toluenesulfonic acid ring protons superimposed over some —N—H's), −7.38 (singlet, benzyl rings' protons) ppm (TMS).

Anal. Calcd. for: $C_{26}H_{33}N_5O_4 \cdot C_7H_8SO_3 \cdot CH_3OH$: C, 59.7; H, 6.63; N, 10.2; S, 4.69. Found. C, 59.2; H, 6.48; N, 10.3; S,4.46.

The compounds of this invention are useful as anticoagulants, since they inhibit thrombin which they bind. Their anticoagulant activity was determined by measuring thrombin time (TT) utilizing an in vitro test wherein exogenous thrombin is added to oxalated plasma and clotting time is measured in the presence of the test compound. The plasma recalcification time (PRT) was also used in an in vitro test for measuring thrombin inhibition wherein exogenous calcium ions were added to oxalated plasma (the system makes its thrombin in situ), and measuring clotting time in the presence of the compounds.

Following Table I presents in vitro thrombin times for the dipeptide and tripeptide compounds of this invention as compared with the known anticoagulant TAME at the indicated peptide concentrations with the indicated conventional clotting mixture.

TABLE I

In Vitro Thrombin Times<sup>a</sup> for Gly-Pro-Arg and Pro-Arg Derivatives

| Peptide | Thrombin Times (sec) at Peptide Concentrations (mg/ml) | | | | |
|---|---|---|---|---|---|
| | 0.125 | 0.25 | 0.5 | 1.0 | 2.0 |
| Control 15 sec | 0 | 0 | 0 | 0 | 0 |

TABLE I-continued

In Vitro Thrombin Times[a] for Gly-Pro-Arg and Pro-Arg Derivatives

| Peptide | Thrombin Times (sec) at Peptide Concentrations (mg/ml) | | | | |
|---|---|---|---|---|---|
| | 0.125 | 0.25 | 0.5 | 1.0 | 2.0 |
| Boc-Gly-Pro-Arg-OBzl.TsOH (Ex. 3) | 23 | 29 | 42 | 56 | 75 |
| Gly-Pro-Arg-OBzl.TsOH.CF$_3$CO$_2$H (Ex. 4) | 19 | 26 | 44 | 68 | 135 |
| Boc-Pro-Arg-OBzl.TsOH.MeOH (Ex. 1) | 40 | 44 | 73 | 91 | 159 |
| Pro-Arg-OBzl.TsOH.CF$_3$CO$_2$H (Ex. 2) | 19 | 23 | 31 | 46 | 69 |
| Tos-Arg-OMe (TAME) | 24 | 30 | 39 | 68 | 87 |

[a]Clotting mixture: 0.2 ml. oxalated dog plasma, 0.1 ml. barbital buffer containing peptide and 0.1 ml. thrombin (1 unit/ml.)
Boc = t-butyloxycarbonyl
TAME = tosylarginine methyl ester hydrochloride
Bzl = benzyl In the following Table II, PRT (average) for each of the compounds of this invention as compared with TAME anticoagulant are given in seconds.

TABLE II

In Vitro Thrombin Times, Comparisons with TAME

| Conc. Test Compound mg/ml | 0.25 | 0.5 | 1.0 | 1.5 | 2 |
|---|---|---|---|---|---|
| Boc-Gly-Pro-Arg-OBzl. TsOH[a] (Example 3) | 88 | 110 | 146 | 202 | |
| TAME | 105 | 120 | 176 | 203 | 230 |
| Control 66 sec. | | | | | |
| H-Gly-Pro-Arg-OBzl.TsOH. CF$_3$CO$_2$H[a] (Example 4) | 77 | 100 | 198 | 246 | 296 |
| TAME | 96 | 123 | 168 | 220 | 273 |
| Control 55 sec | | | | | |
| Boc-Pro-Arg-OBzl.TsOH. MeOH[a] (Example 1) | 128 | 160 | 207 | 229 | 250 |
| TAME | 105 | 120 | 176 | 203 | 230 |
| Control 66 sec | | | | | |
| H-Pro-Arg-OBzl.TsOH. CF$_3$CO$_2$H[a] (Example 2) | 89 | 102 | 134 | 209 | — |
| TAME | 105 | 120 | 176 | 203 | 230 |
| Control 66 sec | | | | | |
| Z-Pro-Arg-OBzl.TsOH.MeOH [b] (Example 5) | 240 | 270 | 345 | — | 435 |
| TAME | 188 | 210 | 240 | — | 285 |
| Control 115 sec. | | | | | |

[a]Clotting Mixture:
0.2 ml. oxalated dog plasma
0.1 ml. Barbital buffer saline containing test compound
0.1 ml. CaCl$_2$ 0.025 M
Z = benzyloxycarbonyl
Bzl = benzyl
TsOH = p-toluenesulfonic acid
[b]Clotting Mixture:
0.1 ml. oxalated dog plasma
0.2 ml. Barbital buffer saline containing test compound
0.1 ml. CaCl$_2$ 0.025 M

What is claimed is:

1. A C-terminal- or C-terminal- and N-terminal-protected lower peptide of the class of dipeptide and tripeptide salts of a pharmaceutically-acceptable acid wherein the dipeptide moiety is L-prolyl-L-arginine and the tripeptide moiety is glycyl-L-prolyl-L-arginine and a methanolate solvate thereof, wherein the C-terminal protective group is benzyl and the N-terminal protective group is benzyloxycarbonyl or tert.-butyloxycarbonyl.

2. A compound of the group consisting of N-tert-butyloxycarbonyl-L-prolyl-L-arginine benzyl ester p-toluenesulfonate methanolate, L-prolyl-L-arginine benzyl ester p-toluenesulfonate trifluoroacetate, N-tert-butyloxycarbonylglycyl-L-prolyl-L-arginine benzyl ester p-toluene sulfonate, glycyl-L-prolyl-L-arginine benzyl ester p-toluene sulfonate trifluoroacetate and N-benzyloxycarbonyl-L-prolyl-L-arginine benzyl ester p-toluenesulfonate methanolate.

3. The compound of claim 2 which is N-tert-butyloxy-carbonyl-L-prolyl-L-anginine benzyl ester p-toluenesulfonate methanolate.

4. The compound of claim 2 which is L-prolyl-L-arginine benzyl ester p-toluenesulfonate trifluoroacetate.

5. The compound of claim 2 which is N-tert-butyloxycarbonylglycyl-L-prolyl-L-arginine benzyl ester p-toluenesulfonate.

6. The compound of claim 2 which is glycyl-L-prolyl-L-arginine benzyl ester p-toluenesulfonate trifluoroacetate.

7. The compound of claim 2 which is N-benzyloxycarbonyl-L-prolyl-L-arginine benzyl ester p-toluenesulfonate methanolate.

* * * * *

UNITED STATES PATENT AND TRADEMARK OFFICE
CERTIFICATE OF CORRECTION

PATENT NO. : 3,966,701
DATED : June 29, 1976
INVENTOR(S) : Linneaus C. Dorman and Roberta C. Cheng Sheet 1 of 2

It is certified that error appears in the above-identified patent and that said Letters Patent are hereby corrected as shown below:

Title and Abstract page, item [57], second to last line, "butyloxycarbonylglycol-L-prolyl-L-arginine" should read -- butyloxycarbonylglycyl-L-prolyl-L-arginine --.

Column 1, line 23, "screeing" should read -- screening --.

Column 1, line 31, "pro-Arg(prolylarginine)" should read -- Pro-Arg(prolylarginine) --.

Column 1, lines 31 and 32, "com-pounds" should read -- found --.

Column 1, line 33, "cmpounds" should read -- compounds --.

Column 2, line 41, after "100" insert omitted ml..

Column 2, line 43, after "to" insert omitted $\leq$

Column 2, line 25, "$^{+1}$" should read -- $^{-1}$ --.

Column 3, line 5, "D$_6$(DMSO-d-" should read -- d$_6$): --.

Column 3, line 37, "choroformate" should read -- chloroformate --.

Column 3, line 63, the word "by" at the end of the line should be deleted.

Column 3, line 65, "chormatography" should read -- chromatography --.

Column 3, line 68, "(9:1 v/v" should read --(9:1 v/v). --

UNITED STATES PATENT AND TRADEMARK OFFICE
CERTIFICATE OF CORRECTION

PATENT NO. : 3,966,701
DATED : June 29, 1976
INVENTOR(S) : Linneaus C. Dorman and Roberta C. Cheng It is certified that error appears in the above-identified patent and that said Letters Patent are hereby corrected as shown below:

-- Sheet 2 of 2 Sheets --

Column 4, line 36, after "fluoroacetate," delete 3.6.

Column 6, line 18, "$d^{25}$" should read -- $D^{25}$ --.

Column 7, line 16, paragraph beginning "In the" should read -- In --.

Column 8, line 35, Claim 3, second line, "butyloxy-carbonyl-L-prolyl-L-anginine benzyl ester" should read -- butyloxy-carbonyl-L-prolyl-L-arginine benzyl ester --.

Signed and Sealed this

Eleventh Day of January 1977

[SEAL]

Attest:

RUTH C. MASON
Attesting Officer

C. MARSHALL DANN
Commissioner of Patents and Trademarks